US005536658A

United States Patent [19]
Shotts, Jr. et al.

[11] Patent Number: 5,536,658
[45] Date of Patent: Jul. 16, 1996

[54] CHONDROITINASE ATTENUATED EDWARDSIELLA ICTALURI AND A VACCINE FOR PREVENTION OF ENTERIC SEPTICEMIA (ES) IN FISH

[75] Inventors: Emmett B. Shotts, Jr., Athens, Ga.; Richard K Cooper, II, Baton Rouge, La.

[73] Assignee: The University of Georgia Research Foundation, Athens, Ga.

[21] Appl. No.: 965,182

[22] Filed: Oct. 23, 1992

[51] Int. Cl.[6] .............................. C12N 1/21; C12N 1/36; A61K 39/02; A01N 63/00

[52] U.S. Cl. .................................... 435/252.3; 424/235.1; 424/93.2; 424/93.48; 435/245

[58] Field of Search .................................... 424/92, 252.3, 424/245, 92, 932, 93.48, 235.1; 435/252.3, 245

[56] References Cited

PUBLICATIONS

Cooper III, Dis. Abstract International 52:6223 (Abstract only).
Cooper II, Dissertation, pp. 5 & 6, 31.
Henbert et al Dictionary of Immunology 3rd Ed. p. 4.
Joseph C. Newton et al., "Outer Membrane Protein Profiles of *Edwardsiella ictaluri*from Fish," Am J. Vet. Res., (2)51:211–215 (Feb. 1990).
J. C. Newton et al., "Pathology of Experimental Enteric Septicaemia in Channel Fish", *Ictalurus punctatus*(Rafinesque), Following Immersion–Exposure to *Edwardsiella ictaluri, Journal of Fish Diseases*, 12:335–347 (1989).

Joseph C. Newton et al., "Isolation, Characterization, and Molecular Cloning of Cryptic Plasmids Isolated from *Edwardsiella ictaluri,*" Am. J. Vet. Res., (11)49:1856–1860 (Nov. 1988).

Clifford E. Starliper et al., "Isozyme Analysis of *Edwardsiella ictaluri", Microbios Letters*, 37:81–87 (1988).

W. D. Waltman et al., "Biochemical Characteristics of *Edwardsiella ictaluri," Applied and Environmental Microbiology*(1)51:101–104 (1986).

E. B. Shotts et al., "Pathogenesis of Experimental *Edwardsiella ictaluri*Infections in Channel Catfish *(Ictalurus punctatus),*" Can. J. Fish Aquat. Sci. 43:36–42 (1986).

T. Miyazaki et al., "Histopathology of *Edwardsiella ictaluri*in Channel Catfish, *Ictalurus punctatus*(Rafinesque)," *Journal of Fish Diseases*, 8:389–392 (1985).

V. S. Blazer et al., "Pathology Associated with *Edwardsiella ictaluri*in Catfish *Ictalurus punctatus*Rafinesque, and *Danio devario*(Hamilton–Buchanan, 1822)," *J. Fish Biol.*., 27:167–175 (1985).

John P. Hawke et al., "*Edwardsiella ictaluri*sp. nov., the Causative Agent of Enteric Septicemia of Catfish," *International Journal of Systematic Bacteriology*, (4)31:396–400 (Oct. 1981).

*Primary Examiner*—Hazel F. Sidberry
*Attorney, Agent, or Firm*—Needle & Rosenberg

[57] ABSTRACT

The present invention provides a chondroitinase attenuated *Edwardsiella ictaluri* bacteria. Further, this invention provides a vaccine comprising a protective amount of a chondroitinase attenuated strain of *Edwardsiella ictduri* bacteria and a method for protecting a fish from Enteric Septicemia comprising administering the vaccine to the fish.

15 Claims, No Drawings

CHONDROITINASE ATTENUATED EDWARDSIELLA ICTALURI AND A VACCINE FOR PREVENTION OF ENTERIC SEPTICEMIA (ES) IN FISH

This invention was made with government support under University of Georgia Veterinary Medical Experiment Station Funds. The government has certain rights in the invention.

BACKGROUND OF THE INVENTION

1. Field of the Invention

This invention is related to vaccines for fish. In particular, the invention is directed to a vaccine for the prevention of Enteric Septicemia.

2. Background Art

An increase in channel catfish production from less than 6 million pounds in 1970 to more than 200 million pounds in 1985 has led to an increase in accompanying mortality loss due to infectious diseases. Since its first discovery in 1976, *Edwardsiella ictaluri* (EI) has become the leading cause of bacterial fish mortality in commercially raised channel catfish.

EI has been isolated from channel catfish, *Ictalurus punctatus* (Hawke 1979); the green knifefish, *Eigmounia viresceus* (Kent and Lyons 1982); danio, *Danio devario* (Lobb and Rhoades 1987); rosy barb, *Puntius couchouius* (Humphrey et al. 1986); walking catfish, *Clarius batrachus* (Kasornchandra et al. 1986); white catfish, *Ictalurus catus* (Newton et al. 1988); and harlequin tetra, *Rosbara heteromorpha* (Reid and Boyle 1989). This organism causes an acute septicemia (Enteric Septicemia (ES)) in fast-growing fish. Externally, EI can cause hemorrhages of the skin around the mouth and throat, pale gills, exopthalmia, lesions of the fontanelle of the frontal bone of the skull, and small cutaneous lesions on the lateral body surface. Internally, lesions may include hypertrophy of the kidney and spleen, hemorrhage and necrosis of the liver, hemorrhage of adipose tissue, the internal wall of the dorsal musculature, and intestine. Death can occur within 96 hours post injection or up to two weeks after water borne challenge (Hawke 1979). Entry of the organism into the catfish has been shown to occur by both olfactory and intestinal routes (Newton et al. 1989; Saeed 1983; Blazer et al. 1985; Miyazaki and Plumb 1985; Shorts et al. 1986).

While Waltman et al. (1986) proposes that chondroitinase may be a possible contributor to virulence, many other possible factors are also set forth. For example, Newton et al. (1988) allude to possible plasmid versus chromosomal mediated virulence factors, noting the longevity of plasmids pEI1 and pEI2 in EI isolates from channel catfish. Blazer et al. (1985) note the need to access the role of the macrophage in the pathogenesis of ES. The virulence factors for the organism, however, remain unknown (Newton et al. (1988)). Likewise, attempts at producing a viable vaccine have been unsuccessful and antibiotic resistant strains of EI are increasing production costs (Starliper 1991).

Consequently, there exists a need for an effective vaccine against ES. This invention satisfies those needs by identifying a primary virulence factor of EI and by providing a viable vaccine and a method of administration.

SUMMARY OF THE INVENTION

The present invention provides a chondroitinase attenuated *Edwardsiella ictaluri* bacteria. Further, this invention provides a vaccine comprising a protective amount of a chondroitinase attenuated strain of *Edwardsleila ictaluri* bacteria and a method for protecting a fish from Enteric Septicemia comprising administering the vaccine to the fish.

DETAILED DESCRIPTION OF THE INVENTION

The present invention provides a chondroitinase attenuated non-pathogenic strain of EI bacteria. As used herein, the phrase "chondroitinase attenuated" includes the entire class of EI organisms that can be made to carry a down-regulated mutation in chondroitinase activity sufficient to diminish or eliminate the pathogenicity of the EI organism so that the EI can be utilized as a vaccine.

The present invention also provides a strain of EI attenuated by an insertion in the chondroitinase gene. By "insertion" is meant incorporation of a nucleic acid into the genome of the host organism, namely EI. The term "mini-transposon" refers generally to transposons which do not contain a transposase gene within their boundaries.

In the Examples, the insertion is accomplished utilizing a plasmid containing the transposon as the delivery vehicle. However, insertion can also be accomplished by conjugation. In addition, once the location of the chondroitinase gene is determined, one can attenuate the chondroitinase gene by substitution or deletion. Such substitutions or deletions are preferably several base pairs to avoid reversion. Deletion, insertion, or substitution mutations can be made in the gene sequence in either the regulatory or coding region to prevent transcription or to render the transcribed product non-functional or of sufficiently diminished pathogenicity. Techniques for alternative insertions, deletions and substitutions are set forth in Sanbrook et al., *Molecular Cloning: A Laboratory Manual,* 2nd Ed., Cold Spring Harbor Laboratory, Cold Spring Harbor, N.Y. (1989).

Another specific embodiment of the present invention includes a chondroitinase attenuated strain of EI. This strain is identified in the Example as the Mutant Ictaluri Number 15 (MI-15) strain, which is 100% negative for chondroitinase activity and is non-pathogenic in vivo to the catfish, *Ictalurus puntatus.*

The present invention also provides a ehondroitinase attenuated non-pathogenic strain of EI in a pharmaceutically suitable carrier and a vaccine comprising a protective mount of the mutant EI. A "protective amount" is any amount which elicits an immune response sufficient to prevent disease upon challenge with the wild type EI. Immunogenic mounts of a chondroitinase attenuated EI can be determined using standard procedures. Briefly, various concentrations of an EI are prepared, administered to a fish and the immunological response (i.e., morbidity, gross and microscopic pathology, and the production of antibodies) of the fish to each concentration is determined. For example, preferred protective amounts were found to be between about $1\times10^7$ and $1\times10^9$ cfu/ml and especially about $10^8$ cfu/ml.

The pharmaceutically acceptable carrier in the vaccine of the instant invention can comprise water, saline or other suitable carriers (Arnon, R. (Ed.) *Synthetic Vaccines I:*83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). One example of a suitable adjuvant is NaCl, which can enhance the uptake of the organism by the fish. Methods of administration can be per os, by immersion of the fish in the vaccine, or by injection. A preferred immersion time is between about 30 and 60 seconds.

It can be appreciated from the above that the vaccine can be used as a prophylactic or a therapeutic. Thus, the invention provides methods of preventing or treating an EI infection and the associated disease by administering the vaccine to a fish.

The methods described herein can be used for any species of fish which is susceptible to ES. Such fish include channel catfish, *Ictalurus punctatus*; the green knifefish, *Eigmounia viresceus*; danio, *Danio devario*; rosy barb, *Puntius couchouius*; walking catfish, *Clarius batrachus*; white catfish, *Ictalurus catus*; and harlequin tetra, *Rosbara heteromorpha*.

The present invention also provides a method utilizing transpositional mutagenesis to produce a chondroitinase attenuated non-pathogenic strain of EI bacteria. The term "transpositional mutagenesis" is meant to include generally the methods described in the art (see e.g. Kleckner et al., *Methods in Enzymology* 204:139–180 (1991)) whereby transposons are used to produce mutations in microorganisms.

EXAMPLES

Materials and Methods

Bacteria and media. The isolates used in this study were *Edwardsiella ictaluri* strain ALG-91-344 (supplied by Dr. J. Plumb, Auburn University) and *Escherichia coli* DH5alpha F'. These isolates are also commercially available and are on deposit with the ATCC. Transposon Tn903, encoding kanamycin resistance, is carried on the suicide plasmid pNK2794 (also available from Dr. Nancy Kleckner, Department of Biochemistry and Molecular Biology, Harvard University, 7 Divinity Avenue, Cambridge, Mass. 02138). In addition, other strains of *Edwardsleila ictaluri* and *Escherichia coli* can be utilized.

*Escherichia coli* DH5alpha served as the organism from which the plasmid was isolated. All cultures were initially grown in BHI broth with the appropriate antibiotics. Ampicillin at 30 mcg/ml and kanamycin at 45 mcg/ml were used to maintain the plasmid pNK2794 in DH5alpha, while kanamycin alone was used to maintain the transposon in the transformed *E. ictaluri*. Transconjugates and parent strain controls were plated onto Edwardsiella Isolation Media (EIM) (Shotts and Waltman 1990) supplemented with 45 mg/ml kanamycin. Transconjugates were transferred to EIM with kanamycin to insure purity and were stocked in BHI broth with 20% glycerol and held at −20° C. until further characterization could be conducted. SOC media (Sambrook et al. 1989) was used in transformation experiments to allow the transformed cells to recover and express the antibiotic resistance marker before plating on antibiotic containing media.

pNK2794::Tn903 isolation. *Escherichia coli* DH5alpha served as the donor organism for the suicide plasmid pNK2794::Tn903. Competent *E. coli* DH5alpha, made competent by $Ca^{++}$ following the protocol of Sambrook et al. (1989), was transformed by the temperature shock method of Sambrook et al. (1989) with 15 ng of plasmid (supplied by Dr. Mark Jackwood, Poultry Disease Research Center, Athens, Ga.) containing the transposon. Transformed cells were suspended in 1 ml of SOC media for 1 hour before plating onto BHI agar with ampicillin and kanamycin. Parent strain *E. coli* DH5alpha was also plated on the BHI agar with ampicillin and kanamycin as a negative control. All cultures were grown overnight at 37° C. Colonies growing on the antibiotic containing plates were assumed to have accepted the suicide plasmid. One colony was picked and transferred to 500 ml of BHI supplemented with ampicillin and kanamycin and grown on a shaker incubator at 37° C. to an optical density ($OD_{600}$)=0.4 at which time chloramphenicol was added for plasmid amplification (8). The suicide plasmid was isolated by the modified method of Kado and Liu (1981) as described by Cooper (1991) and then purified by cesium chloride density centrifugation (Sambrook et al. 1989). Purified plasmid was stored in TE buffer (10 mM Tris, 1 mM EDTA, pH8.0) at 4° C. until further use.

*Edwardsiella ictaluri* transformation. Competent *E. ictaluri* (made competent as described above) was transformed with 20 ng of pNK2794 using the method described by Sambrook et al. (1989). Transformed cells were suspended in 1 ml of SOC media and incubated for 1 hour at 30° C. to allow expression of the antibiotic marker on the transposon. The bacteria were then plated onto EIM+45 mg/ml kanamycin and incubated overnight at 30° C. Parent strain *E. ictaluri* was plated onto EIM/kanamycin plates as a control. Bacterial colonies were transferred to EIM/kanamycin plates for further characterization.

Phenotypic characterization and extracellular enzyme activity. Kanamycin resistant colonies were screened for the loss of 25 phenotypic characteristics described by Waltman et al. (1986). Ninety-six well microtiter plates were used to screen 500 colonies. Each well was supplied with 150 mcl of the biochemical to be tested and 10 mcl of the mutant to be tested. One well on each plate was not inoculated as a negative control.

Mutants were grouped based on the results of the microtiter assays and random samples from each group were taken and screened for loss of hemolysin and chondroitinase. For the chondroitinase assay, chondroitin sulfate was added into a suitable basal media (an example of such media is BHI media). The media was inoculated with the EI organism and after 5–7 days chondroitinase was assayed by flooding the plates first with 4% bovine serum albumin and allowed to stand for 30 min. Subsequently, the excess was drained and 1.0 N HCl solution was added and the plates were incubated additionally for 30 min. Chondroitinase activity is seen as a clear area around the bacterial colonies against a cloudy background. Fifteen motants (designated MI-1 through MI-15) showing a loss of chondroitinase activity were utilized for determining virulence in channel catfish.

Virulence studies using channel catfish. Channel catfish weighing about 5 grams each were acclimated for two weeks in 20 liter aquaria equipped with heaters, undergravel, and outside filters. Each tank contained 15 fish for a total of 45 fish. All fish were handled in accordance with the guidelines set forth by the University of Georgia's policy for animal care.

Two preliminary trials and 1 full replication were conducted to determine the loss of virulence of the mutant organism. In each trial, Mutant MI-15 containing the transposen and the parent strain were grown in BHI broth for 18 hours, centrifuged, pellets washed in 0.65% saline, centrifuged, and the pellet resuspended to an $O.D._{600}=0.80+0.05$. Fish were injected intraperitoneally with $1\times10^8$ cells with MI-15 and the parent strain, respectively. Fish were held for 2 weeks and observed for mortality. After two weeks, fish injected with MI-15 and naive fish were challenged intramuseularly with $3\times10^8$ cells of the parent strain of *E. ictaluri* prepared as described above. Fish were observed for mortality and the kidney of moribund fish were cultured to both blood agar and EIM with and without 45 mcg/ml of kanamycin to screen for the presence of both mutant and wild type *E. ictaluri*.

Southern blot analysis. Southern blots were performed on both the mutant strain MI-15 and the parent strain of *E. ictaluri*. Genomic DNA was harvested as described by Ausubel et al. (1990) and 2 mcg was restricted with the enzymes Sma I and Eco RI in separate reactions as described in the protocol by Sambrook et al. (1989). Plasmid was isolated using the Qiagen$^R$ system (Qiagen, Inc., Studio City, Calif.). Digested chromosomal (2 mcg) and plasmid (1 mcg) DNA of the parent and transconjugate strains was electrophoresed on a 1.0% agarose gel for 6 hours at 50 volts. Lambda DNA (1 mcg) digested with Bcl I served as both the molecular weight marker and the negative control and 2 mcg of undigested pNK2794 served as the positive control for the Southern blot. The blot was conducted following the protocol described by Ausubel et al. (1990) for nylon membrane with a $^{32}$P labelled probe (Ausubel et al. 1990). Tn903 probe DNA was prepared by digesting 306 mcg of pNK2794 with Bam HI, which cuts the outer most ends of the transposon. The digested plasmid was electrophoresed on a 1% agarose gel at 50 volts for 3 hours, the transposon excised from the gel, and purified with GeneClean. The probe (102 mcg) was radioactively labelled for 12 hours at 37° C. using random primers to incorporate $^{32}$P-CTP into the transposon. Hybridization and subsequent washes were conducted under high stringency conditions of low salt (6×SSC) and high temperature (65° C.) as described by Ausubel et al. (1990).

Plasmid comparison: Mutant vs. wild type. Plasmid isolation of the parent strain and transconjugates MI-15, MI-9, and MI-4 was done using the Qiagen plasmid isolation system. A 1.0% agarose gel onto which 500 ng of each plasmid mixture was loaded was done with the isolated plasmids using *E. coli* V517 as a reference marker. The gel was run at 50 volts for 6 hours. Plasmid migrations were observed to determine if the transposon had integrated into either of the two native, cryptic plasmids of *E. ictaluri*, and to ascertain if the suicide plasmid was being maintained in the transconjugate.

Results

Transformation of *E. ictaluri*. Transformed *E. ictaluri* plated onto EIM+45 mcg of kanamycin yielded $3.2 \times 10^2$ kanamycin resistant transformants. Two of these transconjugates were selected for comparison and found to contain stable insertions based upon plating on EIM without kanamycin and then replicating back to EIM/kanamycin after 24 hours to show no loss of kanamycin resistance.

Biochemical and extracellular enzymatic activity. Transconjugates were initially grouped based on loss of phenotypic characteristics that were described by Waltman et al. (1986). These fell into one of four groups: (1) lysine negative, (2) ornithine negative, (3) ribose/ornithine negative, and (4) methyl red negative (see Table 1). From the results of the phenotypic grouping of the transconjugated isolates, random isolates were selected from each group and examined for changes in chondroitinase activity. All mutants were examined for loss of hemolysin, but a non-hemolytic isolate was not obtained. Transconjugates MI-1 through MI-15 (negative for ornithine and chondroitinase activity) did not show a hemolytic zone different from that of the parent strain of *E. ictaluri*. Transconjugates MI-4 and MI-9 showed chondroitinase activity of 41% and 48% respectively, while MI-15 showed 0% activity, but the zones were less than that of the parent strain. The parent strain of EI, ALG-92-344, showed 100% chondroitinase activity.

Plasmid comparison: Mutant vs wild type. Plasmids were screened to confirm that insertion of the transposon did not occur in EI plasmids pEI1 and pEI2. Reference plasmids were compared to MI-15, MI-9, MI-4 and parent EI strain ALG-91-344. All of the native plasmids seemed to have the same migration rate in both the transconiugate and parent strains, strongly suggesting that the 1.85 kb transposon had not inserted into either pEI1 or pEI2. In Lanes 3, 4, and 5, doublets were seen that were probably linearized forms of the two native, cryptic plasmids, but Lane 3 showed the presence of larger plasmids that may have been an insertion into the 5.2 kb native plasmid. MI-15 was the only transconjugate strain in which no larger migrating plasmids could be detected and was also chondroitinase negative, so it was chosen as the isolate to be examined for decreased virulence in channel catfish.

Virulence studies with channel catfish. To determine the virulence of the MI-15 as compared to the parent strain *E. ictaluri*, a channel catfish assay was performed. Fifteen fish per aquarium were inoculated either with the parent strain or the transconjugate MI-15 or as uninoculated controls. Within 4 days, the fish inoculated with the parent stain began showing signs of septicemia and 100% mortality had resulted by Day 6. The fish inoculated with MI-15 were held for 2 weeks without any clinical signs of disease and were then challenged, along with the uninoculated fish as controls, with the parent strain. None of the fish inoculated with MI-15 and then challenged with the wild type showed any signs of Enteric Septicemia of Channel Catfish (ESC), while 100% mortality occurred in the control fish. In this trial and the two preliminary trials, MI-15 provided 100% protection to channel catfish fingerlings challenged with the parent strain.

Southern blot analysis. Southern blot analysis demonstrated a single insert about 3.2 kb in length in comparison to the 4.0 kb undigested plasmid pNK2794 used as a standard and positive control. The $^{32}$P-labelled probe hybridized to pNK2794 on the nylon membrane and the chromosomal DNA digested with EcoR I which cuts the chromosome on either side of the transposon without cutting the transposon. No hybridization was noted between the probe and the parent strain chromosomal DNA, the plasmid DNA isolated from the transconjugate strain, or the Bcl I digest of lambda used as the negative control. It is concluded from the data that the transposon may have inserted a single time in the chromosomni DNA of the transconjugate strain of *E. ictaluri*.

Obtaining viable transconjugates for study was somewhat difficult since $^-10^7$ competent cells results in $^-10^2$ transformants having acquired the transposon marker. A possible explanation for the low number of transformants could be insertion of the transposon into a gene sequence that is critical for survival of the organism. In work with TNphoA it was noted that transposon insertion resulted in amounts of alkaline phosphatase lethal to the transconjugates after only one passage.

Hemolysin activity did not appear altered in any of the mutants isolated. However, the actual zones of hemolysis are so small for *E. ictaluri*, that a quantitative measurement as described by Hsu et al. (1981) is not possible with a high degree of accuracy. A change could be noted in the ability of some of the transconjugates to breakdown chondroitin sulfate, zones smaller than those created by the parent strain were observed. Chondroitinase negative transconjugates when used to inoculate shannel catfish, did not produce disease in channel catfish.

Throughout this application various publications are referenced. Full citations follow the table. The disclosures of these publications in their entireties are hereby incorporated by reference into this application in order to more fully describe the state of the art to which this invention pertains.

The preceding examples are intended to illustrate but not limit the invention. While they are typical of those that might be used, other procedures known to those skilled in the art may be alternatively employed.

TABLE 1

Frequency of phenotypic losses due to transposon insertion

| Phenotype lost* | Number isolated | Percent of total |
|---|---|---|
| Ornithine | 74 | 14.8 |
| Lysine | 115 | 23.0 |
| Ribose | 6 | 1.2 |
| Methyl Red | 24 | 4.8 |
| Orn/Rib. | 148 | 29.6 |
| Orn/Lys. | 33 | 6.6 |
| Lys/Meth. Red | 100 | 20.0 |
| Totals | 500 | 100.0 |

*Based on 500 mutants isolated and screened.

References

Aoki, T., T. Arai, and S. Egusa. 1977. Detection of R plasmids in naturally occurring fish-pathogenic bacteria, *Edwardsiella tarda*. Microbiol Immunol. 21:77–83.

Aoki, T., S. Egusa, and T. Arai. 1974. Detection of R factors in naturally occurring *Vibrio anguillarm* strains. Antimicrob. Agents Chemother. 6:534–538.

Aoki, T., S. Egusa, Y. Ogata, and T. Watanabe. 1971. Detection of resistance factors in fish patbogen *Aeromonas liquefaciens*. J. Gen. Microbiol. 65:343–349.

Aoki, T., S. Egusa, and T. Watanabe. 1973. Detection of R + bacteria in cultured marine fish, Yellowtail (*Seriola quinqueradiata*). Jpn. J. Microbiol. 17:7–12.

Aoki, T., Y. Jo, and S. Egusa. 1980. Frequent occurrence of drug resistant bacteria in ayu (*Plecoglossus altivelis*) culture. Fish Pathol. 15:1–6.

Aoki, T., T, Kitao, and K. Kawano. 1981. Changes in drug resistance of *Vibrio anguillarum* in cultured ayu (*Plecoglossus altivelis*). J. Fish Dis. 4:223–230.

Atsuhiro, O., H. Sugisaki, and M. Takanami. 1981. Nucleotide sequence of the kanamycin resistance transposon Tn903. J. Mol. Biol. 147:217–226.

Ausubel, F. M., R. Brent, R. E. Kingston, D. D. Moore, J. G. Seidman, J. A. Smith, and K. Struhl. 1990. Current protocols in molecular biology. Massachusetts General Hospital and Harvard Medical School.

Blazer, V. S., E. B. Shotts, W. D. Waltman. 1985. Pathology associated with *Edwardsida ictaluri* in catfish (*Ictalurus punctatus*) and danio (*Danio deverio*). J. Fish Biol. 27:167–176.

Ely, B. 1985. Vectors for transposon mutagenesis of nonenterric bacteria. Mol. Genes and Genetics 200:302–304.

Gaillard, J. L., P. Berche, and P. Sansonetti. 1986. Transposon mutagenesis as a tool to study the role of hemolysin in the virulence of *Listeria monocytogenes*. Infect. and Immun. 52:50–55.

Gavini, F., D. Izard, P. A. Trinel, B. Lefebwe, and H. Leclerc. 1981. Etude taxonomique d'entbacteries appartenant ou apparantees a l'erpece *Escherichia coli*. Can. J. Microbiol. 27:98–106.

Grindley, N., and C. M. Joyce. 1980. Genetic and DNA sequence analysis of the kanamycin resistance transposon Tn903. Proc. Natl. Acad. Sci. 77:7176–7180.

Hawke, J. P. 1979. A bacterium associated with disease of pond cultured catfish, *Ictalurus punctatus*. J. Fish. Res. Board Can. 36:1508–1512.

Hawke, J. P., A. C. McWhorter, A. G. Steigenvalt, and D. J. Brenner. 1981. *Edwardsiella ictaluri* sp. nov., the causative agent of enteric septicemia of catfish. Int. J. Syst. Bact. 31:396–400.

Hsu, T. C., W. D. Waltman, and E. B. Shotts. 1981. Correlation of extracellular enzymatic activity and biochemical characteristics with regard to virulence of *Aeromonas hydrophila*. Dev. Biol. Stand. 49:101–111.

Humphrey, J. D., C. Lancaster, N. Gudkovs, and W. McDonald. 1986. Exotic bacterial pathogens *Edwardsiella tarda* and *Edwardsiella ictaluri* from ornamental fish *Betta splendens* and *Puntius conchronius*, respectively: Isolation and quarantine significance. Australian Vet. J. 63:369–371.

Jiang, B., and S. P. Howard. 1991. Mutagenesis and isolation of *Aeromonas hydrophila* genes which are required for extracellular excretion. J. Bacteriol. 173:1241–1249.

Kado, C. I., and S. T. Liu. 1981. Rapid procedure for detection and isolation of large and small plasmids. J. Bacteriol. 145:1365–1373.

Kasornchandra, J. D., C. Lancaster, N. Gudkovs, and W. McDonald. 1986. *Edwardsiella ictaluri* from walking catfish, *Clarius batrachus* L. Thailand. J. Fish Dis. 10:137–138.

Kent, M. L., and J. M. Lyons. 1982. *Edwardsiella ictaluri* in the green knife fish, *Eigemannia virescens*. Fish Health News 2:ii.

Kleckner, N., J. Bender, and S. Gottesman. 1991. Uses of transposons with emphasis on Tn10. Methods in Enzymology. 204:139–180.

Leung, K. Y., and R. M. W. Stevenson. 1988a. Tn5-induced protease-deficient strains of *Aeromonas hydrophila* with reduced virulence in fish. Infect. Immun. 56:2639–2644.

Lobb, C. J., and M. Rhoades. 1987. Rapid plasmid analysis for identification of *Edwardsiella ictaluri* from infected channel catfish. Appl. Env. Microbiol. 53:1267–1272.

Marcina, F. L., D. J. Kopecko, K. R. Jones, D. J. Ayers, and S. M. McCowen. 1978. A multiple plasmid-containing *Escherichia coli* strain: Convenient source of size reference plasmid molecules. Plasmid, 1:417–420.

Miyazald, T., J. A. Plumb. 1985. Histopathology of *Edwardsiella ictaluri* in channel catfish *Ictalurus punctatus* (Rafinesque). J. Fish Dis. 8:389–392.

Newton, J. C., R. C. Bird, W. T. Blevins, G. R. Wilt, and L. G. Wolfe. 1988. Isolation, characterization, and molecular cloning of cryptic plasmids isolated from *Edwardsiella ictaluri*. Am. J. Vet. Res. 19:1856–1860.

Newton, J. C., W. T. Blevins, G. R. Wilt, and L. G. Wolfe. 1990. Outer membrane profiles of *Edwardsiella ictaluri* from fish. Am. J. Vet. Res. 51:211–215.

Newton, J. C., L. G. Wolfe, J. M. Grizzle, and J. A. Plumb. 1989. Pathology of experimental enteric septicemia in channel catfish, *Ictalurus punctatus*, following immersion-exposure to *Edwardsiella ictaluri*J. Fish Dis. 12:335–347.

Nomura, N., H. Yamagishi, and A. Oka. 1978b. Gene 3:39–52.

Reid, W. S., and J. A. Boyle. 1989. Plasmid homologies in *Edwardsiella ictaluri*. Appl. Environ. Microbiol. 55:3253–3255.

Saeed, M. O. 1983. Chemical characterization of the lipopolysaccharide of *Edwardsiella ictaluri* and the immune response to this fraction and to whole cell antigen with histopathologic comparison. Doctoral dissertation, Auburn University, Auburn, Ala., 80 pages.

Sambrook, J., E. F. Fritsch, and T. Manniatis. 1989. Molecular cloning: A laboratory manual. Cold Spring Harbor Laboratory, Cold Spring Harbor, N.Y.

Shotts, E. B., V. S. Blazer, W. D. Waltman. 1986. Pathogenesis of experimental infections in channel catfish (*Ictalurus punctatus*). Can. J. Fish Aquatic Sci. 43:36–42.

Speyerer, P. D., and J. A. Boyle. 1987. The plasmid profile of *Edwardsiella ictaluri*. J. Fish Dis. 10:461–469.

Stapleton, M. J., K. S. Jagger, and R. L. Warren. 1984. Transposon mutagenesis of *Pseudomonas aeruginosa* exoprotease genes. J. Bacteriol. 157:7–12.

Starliper, C. E., R. K. Cooper, E. B. Shotts. 1991. Plasmid mediated Romet resistance. Submitted.

Starliper, C. E., W. B. Schill, E. B. Shotts, and W. D. Waltman. 1988. Isozyme analysis of *Edwardsiella ictaluri*. Micobios. Letters 37:81–87.

Taylor, R. K., C. Manoil, and J. J. Mekalanos. 1989. Broad-host-range vectors for delivery of TnphoA: Use in genetic analysis of secreted virulence determinants of *Vibrio cholerae*. J. Bacteriol. 171:1870–1878.

Waltman, W. D., E. B. Shotts, and T. C. Hsu. 1986. Biochemical characteristics of *Edwardsida ictaluri*. Appl. Environ. Microbiol. 51:101–104.

Waltman, D. W., E. B. Shotts, and R. E. Wooley. 1989. Development and transfer of plasmid-mediated antimicrobial resistance in *Edwardsiella ictaluri*. Can. J. Aquat. Sci. 46:1–4.

Weete, J. D., W. T. Blevins, and S. Chitrakorn. 1988. Chemical characterization of lipopolysaccharide from *Edwardsiella ictaluri*, a fish pathogen. Can. J. Micrbiol. 34:1224–1229.

What is claimed is:

1. An isolated, chondroitinase attenuated, non-pathogenic strain of *Edwardsiella ictaluri* bacteria.

2. The bacteria of claim 1, wherein the chondroitinase is attenuated by an insertion of nucleic acid into a chondroitinase gene.

3. The bacteria of claim 1, wherein the bacteria is designated an MI-15 strain.

4. The bacteria of claim 1, in a pharmaceutically suitable carrier.

5. A vaccine comprising a protective amount of the bacteria of claim 4.

6. The vaccine of claim 5, wherein the protective amount is between about $1 \times 10^7$ and $1 \times 10^9$ cfu/ml.

7. The vaccine of claim 6, wherein the protective amount is about $1 \times 10^8$ cfu/ml.

8. The vaccine of claim 5, wherein the carrier is water.

9. The vaccine of claim 5, further comprising an adjuvant.

10. A method of protecting a fish from enteric septicemia comprising administering the vaccine of claim 5, to the fish.

11. The method of claim 10, wherein the fish is a catfish.

12. The method of claim 10, wherein the administering step comprises immersing the fish in the vaccine.

13. The method of claim 12, wherein the fish is immersed in the vaccine for about 30–60 seconds.

14. The method of claim 10, wherein the administering step comprising spraying a fish feed with the vaccine and administering the feed to the fish.

15. A method of making a non-pathogenic strain of *Edwardsiella ictaluri* bacteria comprising utilizing transpositional mutagenesis with a mini-transposon derived from Tn903 to obtain a chondroitinase attenuated *Edwardsiella ictaluri* bacteria.

* * * * *